(12) United States Patent
Ragsdale (10) Patent No.: US 7,576,549 B2
(45) Date of Patent: Aug. 18, 2009

(54) METHODS FOR MEASURING SAMPLE RESISTANCE IN ELECTROPORATION

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 144 days.

(21) Appl. No.: 11/567,438

(22) Filed: Dec. 6, 2006

(65) Prior Publication Data

US 2008/0076144 A1    Mar. 27, 2008

Related U.S. Application Data

(60) Provisional application No. 60/826,422, filed on Sep. 21, 2006.

(51) Int. Cl.
*G01R 27/08* (2006.01)
*A61B 18/04* (2006.01)
*C12M 1/42* (2006.01)

(52) U.S. Cl. .................. 324/711; 324/691; 606/34; 435/285.2

(58) Field of Classification Search .......... 324/711; 435/285.2; 606/34
See application file for complete search history.

(56) References Cited

U.S. PATENT DOCUMENTS

| | | | |
|---|---|---|---|
| 4,471,276 A | 9/1984 | Cudlitz | |
| 4,484,122 A | 11/1984 | Day et al. | |
| 4,520,296 A | 5/1985 | Lepper et al. | |
| 4,540,944 A | 9/1985 | Watanabe | |
| 5,027,083 A | 6/1991 | Kutzavitch et al. | |
| 5,170,429 A * | 12/1992 | Stocklin et al. | 379/395.01 |
| 5,269,937 A * | 12/1993 | Dollinger et al. | 210/656 |
| 5,363,070 A | 11/1994 | Arimoto | |
| 5,642,035 A | 6/1997 | Ragsdale | |
| 5,656,926 A | 8/1997 | Ragsdale | |
| 5,729,426 A | 3/1998 | Ragsdale | |
| 5,891,179 A * | 4/1999 | Er et al. | 607/27 |
| 5,922,282 A * | 7/1999 | Ledley | 422/50 |
| 6,356,086 B1 * | 3/2002 | Cook et al. | 324/659 |
| 6,771,082 B2 | 8/2004 | Ragsdale et al. | |

(Continued)

FOREIGN PATENT DOCUMENTS

WO    WO 2004/050866 A1    6/2004

OTHER PUBLICATIONS

U.S. Appl. No. 11/567,373, filed Dec. 6, 2006.

(Continued)

*Primary Examiner*—Vincent Q Nguyen
*Assistant Examiner*—Jeff Natalini
(74) *Attorney, Agent, or Firm*—Townsend and Townsend and Crew LLP; David B. Raczkowski (57) ABSTRACT

Systems and methods of measuring resistances of samples to be electroporated and utilizing the measured resistances in the electroporation are provided. During an electrical pulse sent to the sample, a time and a corresponding voltage drop on a known capacitance is measured to determine the sample resistance. A constant voltage may be assumed, and the voltage drop across a known resistance in series with the sample resistance is used to determine the sample resistance. Based on the value of the sample resistance, an electrical pulse may be altered by changing a value of a parallel resistance.

24 Claims, 4 Drawing Sheets

U.S. PATENT DOCUMENTS

| | | |
|---|---|---|
| 6,798,175 B2 | 9/2004 | Hanada et al. |
| 6,856,119 B2 | 2/2005 | Crawford |
| 7,054,685 B2 | 5/2006 | Dimmer et al. |
| 2003/0026092 A1 | 2/2003 | Reese et al. |
| 2003/0214269 A1 | 11/2003 | Shiue |
| 2004/0171962 A1* | 9/2004 | Leveque et al. ............ 600/547 |
| 2005/0052630 A1* | 3/2005 | Smith et al. .................. 355/53 |
| 2006/0115888 A1 | 6/2006 | Gamelin et al. |
| 2007/0188181 A1* | 8/2007 | Karges et al. ............... 324/691 |
| 2007/0194759 A1 | 8/2007 | Shimizu et al. |
| 2008/0024079 A1 | 1/2008 | Matsubara et al. |

OTHER PUBLICATIONS

U.S. Appl. No. 60/826,422, filed Sep. 21, 2006.
U.S. Appl. No. 11/857,679, filed Sep. 19, 2007.

* cited by examiner

METHODS FOR MEASURING SAMPLE RESISTANCE IN ELECTROPORATION

CROSS-REFERENCES TO RELATED APPLICATIONS

The present application is related to the following commonly-assigned concurrently filed U.S. patent applications: Ser. No. 11/567,373, entitled "MULTI-CHANNEL ELECTROPORATION SYSTEM," by Ragsdale (hereinafter Ragsdale I), which is incorporated herein by reference for all purposes.

The present application is also related to the following commonly-assigned U.S. Provisional Patent Application No. 60/826,422 entitled "RESISTOR PULSE MODULATION," by Ragsdale, filed Sep. 12, 2006, which is incorporated herein by reference for all purposes.

BACKGROUND

The present invention relates generally to electroporation systems and more particularly to systems and methods for measuring resistances of samples to be electroporated and utilizing the measured resistances in the electroporation.

It is known that exposure of cells or other biological molecules to intense electric fields for brief periods of time temporarily destabilizes membranes. This effect has been described as a dielectric breakdown due to an induced transmembrane potential, and has been termed "electroporation". Among the procedures that use electroporation are the production of monoclonal antibodies, cell-cell fusion, cell-tissue fusion, insertion of membrane proteins, and genetic transformation.

The cells or tissue are exposed to electric fields by administering one or more direct current pulses. These pulses are administered in an electrical treatment that results in a temporary membrane destabilization with minimal cytotoxicity. The intensity of the electrical treatment is typically expressed in terms of the field strength of the applied electric field. This electric field strength is defined as the voltage applied to the electrodes divided by the distance between the electrodes. Electric field strengths used in electroporation typically range from 1000 to 5000 V/cm.

For efficient electroporation, it is necessary to control the shape, e.g. time constant of the electrical pulse. For example, electroporation itself occurs within a narrow range of parameters, such as pulse voltage and pulse duration, which is exhibited by a narrow window between electrocution and little or no electroporation. If a pulse with too long a duration or too high a field strength is used, the cells may be lysed (destroyed). If the duration or field strength of a pulse is too low, electroporation efficiency is lost. As an added difficulty, the optimal voltage and time constant varies with the type of cell. The current emphasis on using electroporation to study cells that are sensitive and difficult to transfect (move molecules through membrane) makes the control of electroporation conditions particularly important.

One problem in selecting the electroporation parameters is that the sample itself (cells plus buffer) is a significant factor in the load imposed on an electroporation system and can have a wide range of resistance values. The sample resistance cannot be measured using a DC current as the sample is polar, and the measurement could disturb the cells. Also, if one did measure the sample resistance using DC, the value determined would be much higher than the actual resistance. Prior art makes these measurements with additional circuitry that uses a low-voltage AC (20 KHz) current. However, the circuit is costly and cannot be used with certain electroporation systems, as described in Ragsdale I.

It is, therefore, desirable to provide systems and methods of measuring sample resistances with fewer parts, at a lower cost, and that are not restricted to using an AC current.

BRIEF SUMMARY OF THE INVENTION

The present invention provides systems and methods of measuring resistances of samples to be electroporated and utilizing the measured resistances in the electroporation. These systems and methods employ one or more techniques such as, during an electrical pulse sent to the sample, measuring a time and a corresponding voltage drop on a known capacitance to determine the sample resistance; assuming a constant voltage and using the voltage drop across a known resistance in series with the sample resistance to determine the sample resistance; and altering an electrical pulse to the sample resistance based on the value of the sample resistance by changing a value of a parallel resistance.

According to an exemplary embodiment, a resistance $R_S$ of a sample load in an electroporation system is estimated. A capacitance C of one or more capacitors is determined. The capacitance C may be obtained by reading an individual capacitance of each of the capacitors from a memory. The capacitors may be selected based on the individual capacitances read from memory. An electrical pulse, e.g. an exponentially decaying pulse or an approximated square wave, is transmitted from the capacitors to the sample load. An initial voltage $V_I$ is measured on the capacitors, which may be donea t any time. At a time $T_1$ after measuring $V_I$, a second voltage $V_2$ is measured on the capacitors. A first estimate of $R_S$ is calculated based on C, $V_I$, $V_2$, and $T_1$.

In one embodiment, a set $R_O$ of resistances of one or more resistive elements other than the sample load are determined. $R_O$ may include a variable resistance connected in parallel with the sample load. The first estimate may also be calculated based on resistances $R_O$. In one aspect, a formula $$T_1 = R \cdot C \cdot \ln\left[\frac{V_I}{V_2}\right]$$

is used to calculate the first estimate of $R_S$, where resistance R includes contributions from $R_S$ and resistances $R_O$. The values for $$\ln\left[\frac{V_I}{V_2}\right]$$

may be obtained by reading approximate values from a table.

In another embodiment, one or more additional voltages are measured on the capacitors at one ore more additional times after measuring $V_I$. An average estimate of $R_S$ may then be calculated based on the first estimate and the additional voltages and additional times. In one aspect, additional estimates of $R_S$ are calculated based on the additional voltages and additional times, and the additional estimates and the first estimate are averaged to obtain the average estimate.

According to another exemplary embodiment, a resistance $R_S$ of a sample load in an electroporation system is estimated. A capacitance C of one or more capacitors is determined. A resistance $R_1$ of one or more resistive elements connected in series with the sample load is determined. An electrical pulse is transmitted from the capacitors to the sample load and to the resistive elements. In one aspect, the electrical pulse has a width of less than 1 millisecond. A voltage $V_C$ is measured on the capacitors. A second voltage $V_2$ that results from a voltage drop is measured. The voltage drop may be after the sample load or the resistive elements. A first estimate of $R_S$ can then be calculated based on C, $R_1$, $V_C$, and $V_2$.

In one embodiment, the calculation of the first estimate of $R_S$ uses a formula for a voltage divider. The voltage divider formula may also utilize a resistance $R_O$ of the electroporation system other than the sample load and $R_1$. The resistance $R_O$ may be connected in parallel with the sample load.

In one embodiment, the resistance $R_1$ is connected in series between the capacitors and the sample load. The second voltage $V_2$ may then be measured between the resistance $R_1$ and the sample load. A switch may be closed to transmit the electrical pulse, and the resistance $R_1$ may include the switch. In another embodiment, the resistance $R_1$ is connected in series between the sample load and a common return path. The second voltage $V_2$ may then be measured after the sample load.

According to another exemplary embodiment, an electrical pulse transmitted to a sample load is altered. A first estimate of a resistance $R_S$ of the sample load is obtained. A variable resistance device, connected in parallel with the sample load, is set to have a first resistive value. The resistive value of the variable resistance device may be set by changing a pulse width of a pulse modulated signal that is sent to the variable resistance device. An electrical pulse is transmitted to the sample load and to the variable resistance device. A second estimate of $R_S$ is then obtained. Based on the second estimate, the variable resistance device is set to have a second resistive value, thereby altering the transmitted electrical pulse. The transmitted electrical pulse may be altered by changing the time constant of the electrical pulse.

In one embodiment, the first estimate is obtained by transmitting a first electrical pulse. Obtaining the first estimate of $R_S$ may include: determining a capacitance C of one or more capacitors; determining a resistance $R_1$ of one or more resistive elements connected in series with the sample load; transmitting a first electrical pulse from the capacitors to the sample load and to the resistive elements; measuring a voltage $V_C$ on the capacitors; measuring a second voltage $V_2$ that results from a voltage drop after at least one of the sample load and the resistive elements; and calculating the first estimate of the resistance $R_S$ of the sample load based on C, $R_1$, $V_C$, and $V_2$.

In another embodiment, the second estimate of $R_S$ may utilize the transmitted electrical pulse and include: determining a capacitance C of one or more capacitors; measuring an initial voltage $V_I$ on the capacitors; measuring a second voltage $V_2$, after a time $T_1$, on the capacitors; and calculating a first estimate of the resistance of the sample load based on C, $V_I$, $V_2$, and $T_1$.

Reference to the remaining portions of the specification, including the drawings claims and Appendices, will realize other features and advantages of the present invention. Further features and advantages of the present invention, as well as the structure and operation of various embodiments of the present invention, are described in detail below with respect to the accompanying drawings.

DETAILED DESCRIPTION OF THE INVENTION

The present invention provides systems and methods for measuring the resistances of sample loads within an electroporation system. In one aspect, additional circuitry, other than circuitry already necessary for electroporation, is not required. In one embodiment, the knowledge of the capacitances, other resistances, and a voltage drop over time during an electrical pulse is used to measure the resistance. In another embodiment, the knowledge of the capacitances and a voltage drop over a known resistance is used to measure the resistance. Additionally, knowledge of the sample resistance may be used to alter the waveform of the delivered electrical pulse.

Figure 1:
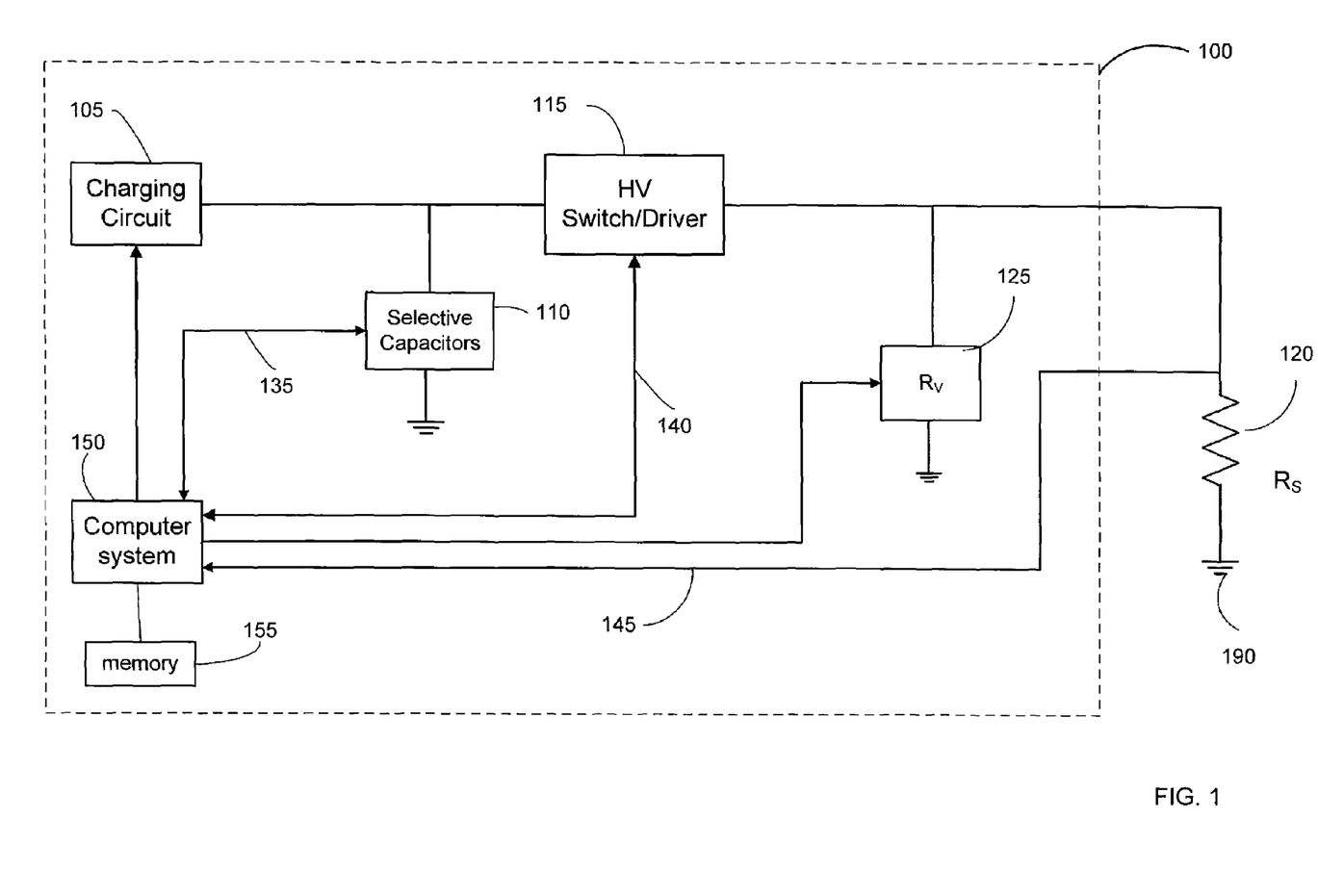
FIG. 1 illustrates an electroporation system according to an embodiment of the present invention.

FIG. 1 illustrates an electroporation system 100 according to an embodiment of the present invention. Lines indicate electrical connections and arrows indicate the flow of information, such as control signals or data. System 100 produces an electrical signal for sample load 120. Computer system 150 receives input parameters for the electrical signal. Computer system 150 may include one or more processors, memory such as RAM, a user interface, and docking ports for receiving external memory units, such as a CD or DVD. The processors may be simple microcontrollers or more complex central processing units.

Based on the input parameters, computer system 150 selects one or more capacitors 110 from a set of available capacitors to achieve a desired capacitance. In one embodiment, electrolytic capacitors are used. Parameters include (a) waveform (exponential or square wave); (b) voltage 10-500V; (c) capacitance (25-3275-mfd); and (d) parallel resistance (50-1000 ohms). In one embodiment, memory element 155 contains the capacitance value of each capacitor in the set. Memory element 155 may be flash RAM or any other suitable memory device. Computer system 150 then may select the capacitors that add up to the desired capacitance.

A charging circuit 105 is connected with capacitance 110 so as to charge capacitance 110 when switch 115, e.g. a high voltage (HV) switch, is open. In one aspect, charging circuit 105 is a power supply or some other constant power source. HV switch 115 connects capacitance 110 to sample load $R_S$ 120 and a variable resistor $R_V$ 125, which is connected in parallel with $R_S$ 120. HV switch 115 may also be a driver with programmable parameters, such as number of pulses, pulse duration, and bursts of pulses.

Charging circuit 105 receives instructions from computer system 150, which may monitor the voltage at capacitor 110, e.g., via a communication line 135. The instructions may include whether to continue to charge capacitance 110 or at what level to charge it. In one embodiment, when the voltage at capacitance 110 reaches a sufficient value, computer system 150 signals a HV driver 115 to connect capacitance 110 to the load sample $R_S$ 120 and variable resistor device 125.

Once charging circuit 105 charges the capacitor 110 to a desired voltage HV switch 115 is closed, e.g. via a control signal from computer system 150. HV switch 115 may also be a driver with programmable parameters, such as number of pulses, pulse duration, and bursts of pulses. At this point, an electrical signal is transmitted to $R_S$ 120 and to $R_V$ 125. In one aspect the electrical signal is an exponentially decaying pulse, a truncated exponentially decaying pulse, or a square wave signal with droop. In one aspect, the square wave signal with droop is part of an exponentially decaying pulse with a long time constant. After the end of the square wave is reached, the pulse may be sent out through another path to ground. In one aspect, a percentage of the drop of the square wave is output. Typically, values around 10% are preferred.

The value of the resistance of $R_V$ 125 may be tuned to control the electrical signal. For example, for an exponentially decaying pulse, the resistance of $R_V$ 125 may be automatically determined such that a desired time constant τ=CR is substantially equal to the desired pulse duration, wherein $R=(R_S \times R_V)/(R_S+R_V)$ and C is the capacitance of capacitor 110. The time constant may be chosen specifically based on the cells or other type of biomolecules in the sample load. As some cells may be sensitive or hard to transvect, a precisely controlled time constant can promote successful electroporation. $R_V$ 125 may be of any embodiment as described in U.S. Provisional Patent Application No. 60/826422.

In one embodiment, system 100 includes a return driver between load a ground. In one aspect, the return driver prevents the use of an AC signal to be used to measure the sample resistance because with a return driver one does not get a return current as the driver acts as a rectifier. Also, at the low voltages necessary for not damaging the sample the response is non-linear, which causes problems with the measurement. Additionally, one would not want to use a DC current as that could affect the sample and be inaccurate. Accordingly, embodiments of the present invention are suitable for such a system.

Embodiments of the invention use knowledge of the time constant to determine the value of $R_S$. Computer system 150 can monitor a voltage across the selected capacitors 110 and determine the time constant. For example, for exponential waveforms, which typically have 5-30 msec time constants, an RC time constant can be measured. In an example for square waves, a voltage on the selected capacitors 110 can be monitored at the beginning and end of a pulse. The droop and pulse width of the waveform is related to a time constant. Since all of the internal resistances are known, the time constant is known, and the capacitance is known, the sample resistance can be determined.

Figure 2:
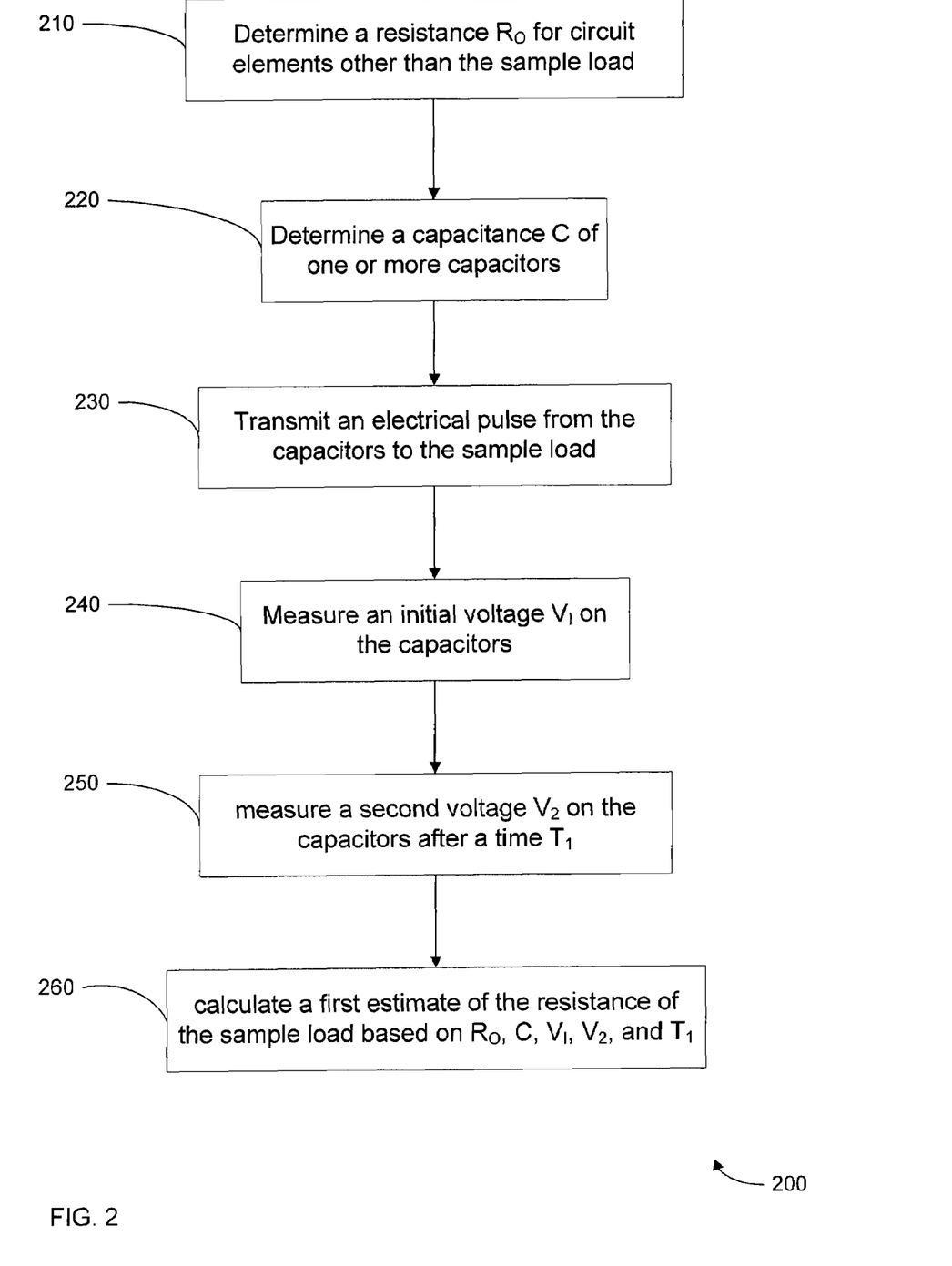
FIG. 2 illustrates a method of measuring sample resistance in an electroporation system according to an embodiment of the present invention.

FIG. 2 illustrates a method 200 of measuring sample resistance in an electroporation system according to an embodiment of the present invention. In step 210, resistances $R_O$ of other resistive elements of the electroporation system other than $R_S$ 120 are determined. The sample load 120 is not the only resistive element between capacitor 110 and ground 190. For example, HV switch 115 and $R_V$ 125 have a resistance. In one embodiment, $R_V$ 125 may not be included in the circuit, and thus its resistance would not be included within $R_O$. Ground 190 may be any common return path that is the zero voltage reference level for the system.

There are other internal resistances as well, such as the internal resistances of the wires, contact-electrode resistance, and connector resistance, which may or may not be negligible. In one embodiment, negligible resistances are neglected, resulting in only a small decrease in accuracy of the resistance measurement. Negligible resistances may thus be defined as resistances for which the inaccuracy of neglecting is acceptable. Accordingly, in some embodiments $R_O$ may be determined to be zero. In another embodiment, an estimate (fudge factor) for the negligible resistances is used. For example, the estimate may include a known resistance per length of similar wires and the approximate length of a wire.

In step 220, a total capacitance C of one or more selected capacitors, which are to be used to deliver an electrical pulse to the sample, is determined. The capacitors may be selected by computer system 150 based on certain input parameters and/or requirements, such as a desired capacitance. For high accuracy, it is important to know the capacitors actual capacitance as most capacitors are only rated to be within 20% of the nominal value.

In one embodiment, the capacitance C is determined by reading the individual capacitance values of the selected capacitors from memory element 155, such as flash RAM or other suitable memory device, and summing these individual values. In another embodiment, the capacitances may be measured by computer system 150, for example, by charging and discharging the selected capacitors through a known resistance, such as $R_V$ 125, and measuring the time constant.

Storing the individual capacitance values may be done as it has been discovered that the capacitors used in, e.g., certain mammalian electroporator systems, do not drift significantly with time. Hence, the capacitors may be measured once, e.g., in the factory, and their values stored in memory element 155. In one aspect, the stored capacitance values are used to select the combination of capacitors that best approximates the desired capacitance.

In step 230, an electrical pulse is transmitted from the selected capacitors to sample load 120. This may be done by sending a control signal from computer system 150 to HV switch 115 after the capacitors have been charged to a desired voltage. Computer system 150 can monitor the voltage across the selected capacitors during the transmission of the electrical pulse.

In step 240, an initial voltage $V_I$ on the selected capacitors is measured. This measurement may be done with monitoring line 135. In one embodiment, the voltage $V_I$ is measured after the electrical pulse is transmitted. In another embodiment, $V_I$ is measured just before the electrical pulse is transmitted. In step 250, a second voltage $V_2$ is measured after a time $T_1$ since voltage $V_I$ was measured.

In one embodiment, there are multiple loads selected by return drivers to ground. If the return drivers are turned-off, the loads are not selected. One can then perform internal tests by charging capacitors and pulsing Rv. This allows any measurement within the capabilities of the system, such as measuring capacitances and determining resistances. In one aspect, this embodiment is used with a high-throughput system incorporating multiple channels. One can then use an embodiment of the present invention to measure the sample resistance without pulsing the sample.

In step 260, a first estimate of the resistance $R_S$ of the sample load 120 is calculated based on $R_O$, C, $V_I$, $V_2$, and $T_1$. In one embodiment, $R_S$ is calculated based on formula (1)

$$T_1 = R \cdot C \cdot \ln\left[\frac{V_I}{V_2}\right],$$

where R is the resistance of the circuit. R includes contributions from $R_S$ and $R_O$. As all of the other quantities are known, $R_S$ may be calculated.

If all of the resistance that include $R_O$ were in series with $R_S$, then $R=R_S+R_O$. If $R_O$ is approximated as being zero then it would not be included in formula (1). If the other resistances $R_O$ involve resistances ($R_{OP}$) in parallel with $R_S$, such as $R_V$ 125, formula (1) would then have a term $(R_{OP} R_S)/(R_{OP}+R_S)$.

One skilled in the art will appreciate that the formula for the total resistance of the circuit may account for any combination of series and parallel resistances.

Formula (1) is derived from the general formula for the time T that it takes for a capacitor starting at a voltage $V_I$ to decrease to a voltage $V_X$ by transmitting charge though a resistance R, which gives formula (2)

$$T = R \cdot C \cdot \ln\left[\left|\frac{V_F - V_I}{V_F - V_X}\right|\right],$$

where $V_F$ is the final voltage of the configuration when the charge on the capacitor is allowed to completely dissipate. In the case of the system being connected to ground and a decaying waveform, the final voltage is zero, which removes $V_F$ from the equation and gives formula (1). When $V_I/V_2=e$, the mathematical constant for the base of the natural logarithm, then equation (1) provides the typical time constant equation of $T_1=(R_S+R_O) \cdot C$, as $\ln[e]=1$.

In one embodiment, "ln[x]", and x, values are stored in a table in memory 155. Note that memory 155 may include multiple memory blocks and/or many different types, such as EEPROM, RAM, flash memory, etc. The table may have a set number of values for x and a corresponding value for ln[x]. Accordingly, computer system 150 may calculate $V_I/V_2$ and then use the nearest "ln[x]" value corresponding to $x \approx V_I/V_2$.

In one embodiment, multiple estimates of the sample resistance are calculated from measuring the voltage across the capacitors at different times. Each data point $[V_X,T_X]$ may be used to determine an estimate of the resistance $R_S$. In one embodiment, the same initial voltage is used. Thus, $T_X$ may be the time it took for the voltage to decrease from $V_I$ to $V_X$. Each of the estimated values for $R_S$ may be summed and averaged in order to obtain an average estimate for $R_S$. In another embodiment, the voltages and times are first averaged and then formula (1) is used to obtain an estimate of the resistance $R_S$. For example, multiple measurements of a voltage may be measured at successive, and closely spaced, times, and the voltage averaged. The time may be set at a point of one of the voltage measurements, in the middle, or at an average of the times. Averages may be simple averages or more complex averages, such as weighted averages.

In one embodiment, the initial voltage changes. The $V_X$ from a last data point may be used as the $V_I$ for the next data point. Each data point $[V_X,T_X]$, where $T_X$ is the time since the last measurement, may be used to determine an estimate of the resistance $R_S$. Each of the estimates values for $R_S$ may be summed and averaged in order to obtain an average estimate for $R_S$.

In some embodiments using a square wave, $V_X$ is the droop voltage (the voltage at the end of the square wave), and $T_1$ is the duration of the square wave. In other embodiments using a square wave, a data point $[V_X,T_X]$ may be taken at any point along the square wave in a similar fashion as for an exponentially decaying waveform.

If the electrical pulse is of a very short duration (e.g., less than 1 msec), the drop in the voltage of the resistors may not be significant, particularly for a square wave. Also, there may not be enough time to sample multiple data points and/or reduce noise. In this case, the voltage may approximated as being constant and the voltage drop across a known resistance may be utilized. This approximation may result in a less accurate determination; however, a benefit is that a quick determination of the sample resistance may be made.

Figure 3:
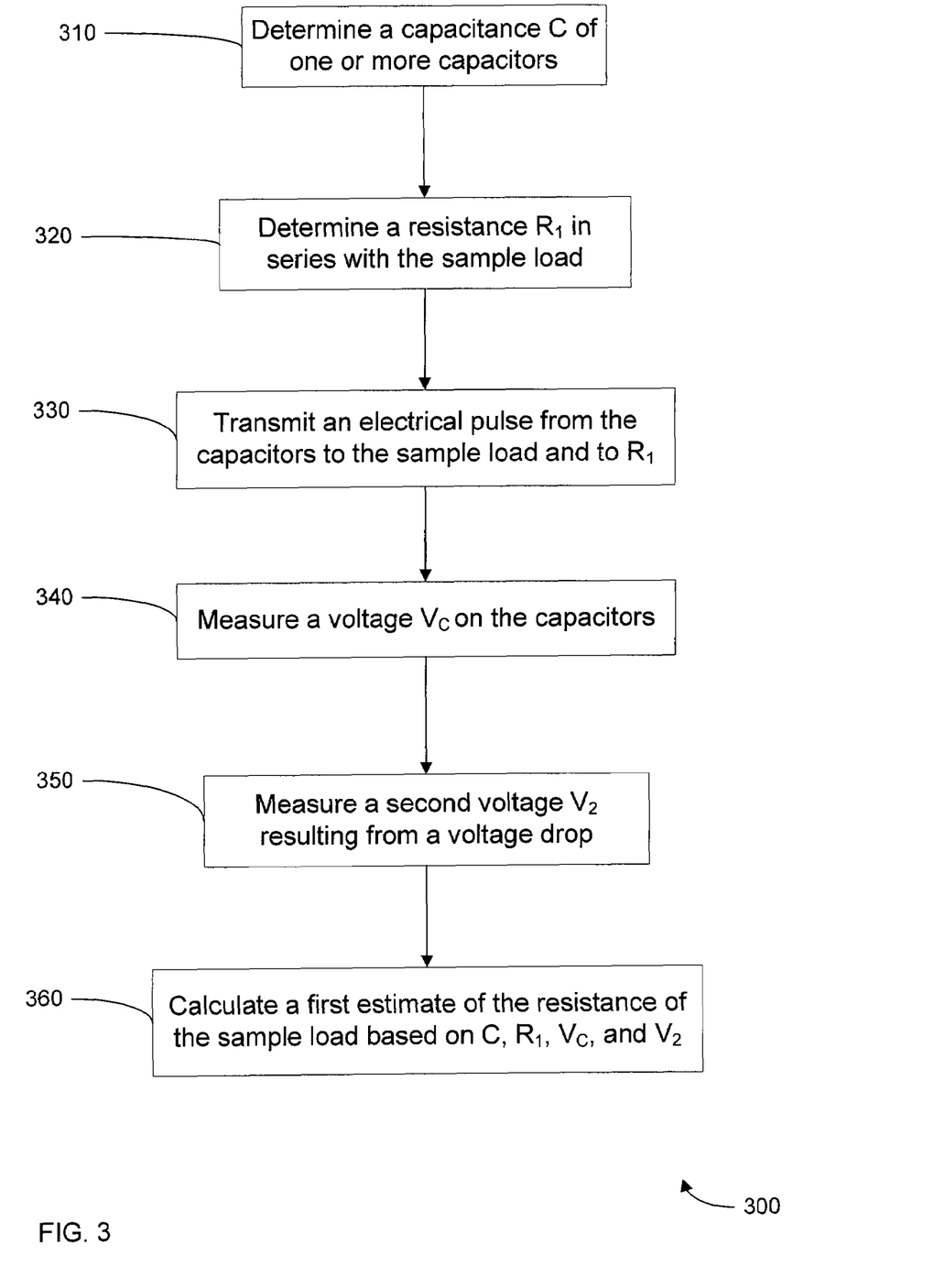
FIG. 3 illustrates a method of measuring sample resistance in an electroporation system according to an embodiment of the present invention.

FIG. 3 illustrates a method 300 of measuring sample resistance in an electroporation system according to an embodiment of the present invention. In step 310, a total capacitance C of one or more selected capacitors, which are to be used to deliver an electrical pulse to the sample, is determined. The capacitance may be determined in a similar manner as in step 220 of method 200.

In step 320, a resistance $R_1$ of one or more resistive elements, connected in series with the sample load, is determined. The resistance $R_1$ may be any resistive element. In one embodiment, the resistance of HV switch 115 is used. In one embodiment, the high-voltage switch contains precision resistors totaling 1 ohm +−1%. A resistance $R_O$ of other circuit elements may also be determined in a similar manner as in step 210 of method 200.

In step 330, an electrical pulse is transmitted from the selected capacitors to the sample load and to the resistance $R_1$. This may be done by sending a control signal from computer system 150 to HV switch 115 after the capacitors have been charged to a desired voltage. The control signal can close the switch so that electrical pulse is transmitted from the selected capacitors to the sample load. Computer system 150 can monitor the voltage across the selected capacitors during the transmission of the electrical pulse.

In step 340, a voltage $V_C$ on the capacitors is measured. This may be done by monitoring line 135. In step 350, a second voltage $V_2$ resulting from a voltage drop is measured. In one embodiment, the voltage drop is after resistance $R_1$. Thus, the second voltage $V_2$ may be measured by monitoring a voltage after the resistance $R_1$. In the embodiment where the resistance $R_1$ is the resistance of HV switch 115, the microprocessor monitors a voltage after the HV switch 115. In one aspect, the voltage after HV switch 115 is measured with monitoring line 140. In another aspect, the voltage after HV switch 115 is measured just before sample load 120, e.g., via monitoring line 145.

In another embodiment, the voltage drop is after sample load 120. In this embodiment, the resistance $R_1$ is connected between sample load 120 and ground 190. For example, the resistance $R_1$ could be a return driver as described in Ragsdale I. In this embodiment, the second voltage may be measured by monitoring a voltage after sample load 120.

In step 360, a first estimate of the resistance of the sample load is calculated based on C, $R_1$, $V_C$, and $V_2$. In one aspect, the formula for a voltage divider is used. For example, in the embodiment where the resistance $R_1$ is HV switch 115, $R_S$ may be calculated with the formula (3)

$$V_2 = \frac{R_S}{R_1 + R_S} V_C.$$

As all of the other quantities are known, $R_S$ may be calculated. In an embodiment where monitoring line 145 is used to measure $V_2$ just before sample load 120, the resistance $R_O$ of the wire or any elements between HV switch 115 and sample load is added to the denominator of formula (3). In another embodiment, resistance $R_1$ includes any resistance $R_O$ of the wire or any elements between HV switch 115 and sample load. In an embodiment where monitoring line 140 is used to measure $V_2$ just after HV switch 115, the resistance $R_O$ of the wire or any elements between HV switch 115 and sample load is added to the numerator and the denominator of formula (3).

In an embodiment, where the resistance $R_1$ is connected between sample load 120 and ground 190, $R_S$ may be calculated with the formula (4)

$$V_2 = \frac{R_S}{R_1 + R_S} V_C.$$

If the other resistances $R_O$ involve resistances in parallel with $R_S$, such as $R_V$ 125, formulas (3) and (4) may be altered accordingly.

In one aspect, method 300 is more suited for small sample resistances. For example, when the relatively low resistance of HV switch 115 is used, higher accuracy is obtained when $R_S$ is small because then the voltage drop to $V_2$ is larger. In another aspect, when the sample has a low resistance, a low voltage pulse (e.g., below 20V), with a short duration, may be used to determine the sample resistance. In this manner, it may be determined whether the sample resistance is too low and that too much current might flow when a normal electrical pulse is used. This might be the case when too many banks (channels) from a multi-channel electroporation system are chosen, as described in Ragsdale I. If the resistance is too low, then fewer banks can be chosen.

Additionally, the knowledge of the sample resistance may be used to alter the parallel resistance $R_V$ 125, e.g., by methods described in U.S. Provisional Patent Application No. 60/826422. $R_V$ 125 can be changed to compensate for an inaccurate initial value (or at least an accuracy that was less than desired) for the resistance of the sample so that the waveform is of the desired shape. For example, the resistance of the sample may be initially approximated, and then after a more accurate measurement has been made, the parallel resistance could be changed to provide the desired time constant or other aspect of the waveform shape.

Figure 4:
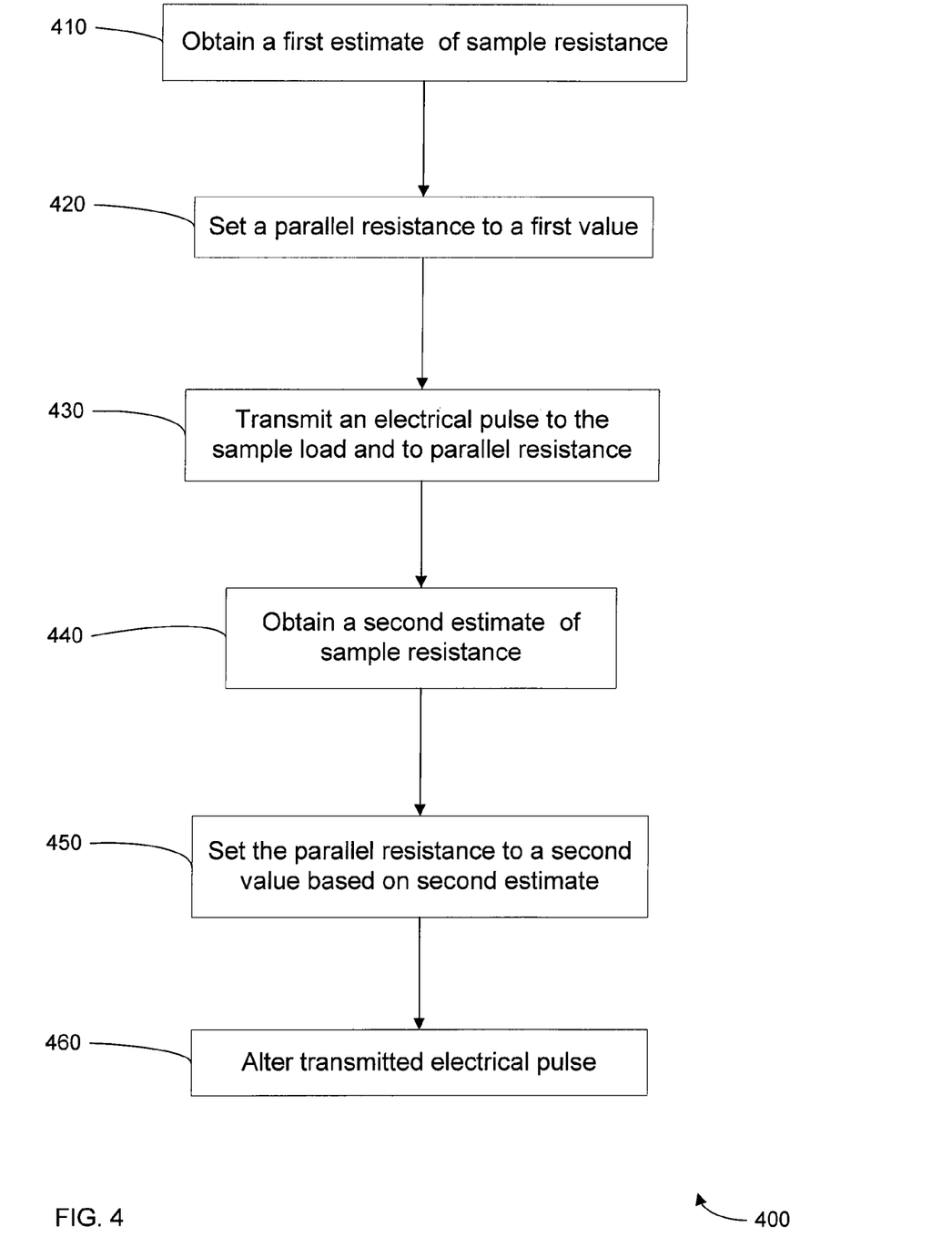
FIG. 4 illustrates a method of altering an electrical pulse transmitted to a sample load according to an embodiment of the present invention.

FIG. 4 illustrates a method 400 of altering an electrical pulse transmitted to a sample load according to an embodiment of the present invention. In step 410, a first estimate for the resistance $R_S$ of the sample load is obtained. In one embodiment, $R_S$ is estimated based on typical values for similar samples. For example, it may be known that samples within a saline solution vary within a particular range of resistance.

In another embodiment, methods 200 or 300 may be used to obtain the first estimate. For example, a low voltage square wave pulse of less than 1 msec duration may be used along with method 300 to obtain the first estimate. Using method 300, a first data point $[V_X, T_X]$ may be used to determine the first estimate.

In step 420, a variable resistance device, which is connected in parallel with the sample load, is set to a first resistive value. The first resistive value may be determined based on input parameters/requirements and the first estimate of the sample resistance. For example, for an exponentially decaying pulse, the resistance of $R_V$ 125 may be automatically determined such that a desired time constant $\tau=CR$ is substantially equal to the desired pulse duration, wherein $R=(R_S \times R_V)/(R_S+R_V)$ and C is the capacitance of capacitor 110. The time constant may be chosen specifically based on the cells or other type of biomolecules in the sample load and parameters input into the electroporation system.

In step 430, an electrical pulse is transmitted to the sample load and to the resistance $R_1$. In one embodiment, the transmission of the electrical pulse was begun before obtaining the first estimate of $R_S$. For example, if the first estimate was obtained using this electrical pulse (e.g., by method 200), the same electrical pulse may continue to be transmitted. In another embodiment, a different electrical pulse is transmitted to obtain the first estimate. For example, if the first estimate was obtained using a low voltage pulse of short duration (e.g., by method 300), the electrical pulse transmitted in step 430 would be a different electrical pulse than the low voltage pulse. In another embodiment, if the first estimate was based on an approximation of typical values, an electrical pulse may not have been previously transmitted up to this point.

In step 440, a second estimate for the resistance $R_S$ of the sample load is obtained. In one aspect, the electrical pulse transmitted in step 430 is used to obtain the second estimate. In one embodiment, method 200 is used to obtain the second estimate. In another embodiment, method 300 is used to obtain the second estimate.

In step 450, the variable resistance device is set to a second resistive value based on the second estimate. The second resistive value may be determined by any method as described herein, and may be based on parameters and/or requirements for the electrical pulse. In one embodiment, the parallel resistance is altered by varying a pulse width modulated signal to one or more switches that are connected in series with a resistor parallel with the sample load, as described in related provisional application 60/826422.

In step 460, the electrical pulse is altered due to the change in the resistance in the variable resistance device. In one aspect, the time constant of the electrical pulse is altered. Other qualities of the electrical pulse, such as voltage, could be altered as well.

While the invention has been described by way of example and in terms of the specific embodiments, it is to be understood that the invention is not limited to the disclosed embodiments. To the contrary, it is intended to cover various modifications and alternatives, in addition to those described above, as would be apparent to those skilled in the art. Therefore, the scope of the appended claims should be understood as encompassing all such modifications and alternatives.

What is claimed is:

1. A method of determining an estimate of a resistance $R_S$ of a sample load in an electroporation system, the method comprising:
   determining a capacitance C of one or more capacitors;
   transmitting an electrical pulse from the capacitors to the sample load in the electroporation system;
   measuring an initial voltage $V_I$ on the capacitors;
   measuring a second voltage $V_2$ on the capacitors, wherein measuring $V_2$ occurs at a time $T_1$ after measuring $V_I$; and
   calculating a first estimate of $R_S$ based on C, $V_I$, $V_2$, and $T_1$.

2. The method of claim 1, further comprising:
   determining a set $R_O$ of resistances of one or more resistive elements other than the sample load, wherein calculating a first estimate is also based on resistances $R_O$.

3. The method of claim 2 wherein calculating the first estimate of $R_S$ comprises using a formula $$T_1 = R \cdot C \cdot \ln\left[\frac{V_I}{V_2}\right],$$

wherein a resistance R includes contributions from $R_S$ and resistances $R_O$.

4. The method of claim 3 wherein the resistances $R_O$ include a variable resistance connected in parallel with the sample load.

5. The method of claim 3 wherein calculating the first estimate of $R_S$ comprises reading an approximate value for $$\ln\left[\frac{V_1}{V_2}\right]$$

from a table.

6. The method of claim 1 further comprising:
measuring one or more additional voltages on the capacitors at one or more additional times after measuring $V_I$; and
calculating an average estimate of $R_S$ based on the first estimate and the additional voltages and additional times.

7. The method of claim 6 wherein calculating an average estimate of $R_S$ comprises:
calculating additional estimates of $R_S$ based on the additional voltages and additional times; and
averaging the additional estimates and the first estimate to obtain the average estimate.

8. The method of claim 1 wherein the electrical pulse approximates a square wave.

9. The method of claim 1 wherein determining a capacitance C of one or more capacitors comprises reading an individual capacitance of each of the capacitors from a memory.

10. The method of claim 9, further comprising selecting the capacitors based on the individual capacitances read from memory.

11. A method of determining an estimate of a resistance $R_S$ of a sample load in an electroporation system, the method comprising:
determining a capacitance C of one or more capacitors;
determining a resistance $R_1$ of one or more resistive elements connected in series with the sample load in the electroporation system;
transmitting an electrical pulse from the capacitors to the sample load and to the resistive elements;
measuring a voltage $V_C$ on the capacitors;
measuring a second voltage $V_2$ that results from a voltage drop after at least one of the sample load and the resistive elements; and
calculating a first estimate of $R_S$ based on C, $R_1$, $V_C$, and $V_2$.

12. The method of claim 11 wherein calculating the first estimate of $R_S$ comprises using a formula for a voltage divider.

13. The method of claim 12 further comprising:
determining a resistance $R_O$ of the electroporation system other than the sample load and $R_1$, wherein the formula includes $R_O$.

14. The method of claim 13 wherein the resistance $R_O$ is connected in parallel with the sample load.

15. The method of claim 11 wherein the resistance $R_1$ is connected in series between the capacitors and the sample load, and wherein the second voltage $V_2$ is measured between the resistance $R_1$ and the sample load.

16. The method of claim 15 further comprising
closing a switch to transmit the electrical pulse, wherein the resistance $R_1$ includes the switch.

17. The method of claim 11 wherein the resistance $R_1$ is connected in series between the sample load and a common return path, and wherein the second voltage $V_2$ is measured after the sample load.

18. The method of claim 11 wherein the electrical pulse has a width of less than 1 millisecond.

19. An electroporation system that determines an estimate of a resistance $R_S$ of a sample load in the electroporation system, the system comprising:
a plurality of capacitors;
a computer system that determines a capacitance C of one or more of the capacitors; and
a switch that is coupled with the computer system and that when open allows transmitting an electrical pulse from the one or more capacitors to the sample load in the electroporation system,
wherein the computer system is configured to:
measure an initial voltage $V_I$ on the one or more capacitors;
measure a second voltage $V_2$ on the one or more capacitors, wherein measuring $V_2$ occurs at a time $T_1$ after measuring $V_I$; and
calculate a first estimate of $R_S$ based on C, $V_I$, $V_2$, and $T_1$.

20. The electroporation system of claim 19, wherein the computer system is further configured to determine a set $R_O$ of resistances of one or more resistive elements other than the sample load, wherein calculating a first estimate is also based on resistances $R_O$.

21. The electroporation system of claim 20, wherein calculating the first estimate of $R_S$ comprises using a formula $$T_1 = R \cdot C \cdot \ln\left[\frac{V_I}{V_2}\right],$$

wherein a resistance R includes contributions from $R_S$ and resistances $R_O$.

22. An electroporation system that determines an estimate of a resistance $R_S$ of a sample load in the electroporation system, the system comprising:
a plurality of capacitors;
a computer system that determines a capacitance C of one or more of the capacitors and that determines a resistance $R_1$ of one or more resistive elements connected in series with the sample load in the electroporation system; and
a switch that is coupled with the computer system and that when open allows transmitting an electrical pulse from the one or more capacitors to the sample load in the electroporation system and to the resistive elements;
wherein the computer system is configured to:
measure a voltage $V_C$ on the capacitors;
measure a second voltage $V_2$ that results from a voltage drop after at least one of the sample load and the resistive elements; and
calculate a first estimate of $R_S$ based on C, $R_1$, $V_C$, and $V_2$.

23. The system of claim 22 wherein calculating the first estimate of $R_S$ comprises using a formula for a voltage divider.

24. The system of claim 23 wherein the computer system is further configured to determine a resistance $R_O$ of the electroporation system other than the sample load and $R_1$, wherein the formula includes $R_O$, and wherein the resistance $R_O$ is connected in parallel with the sample load.

* * * * *